United States Patent
Qu

(10) Patent No.: US 9,668,653 B2
(45) Date of Patent: Jun. 6, 2017

(54) QUANTIFICATION OF UNDER-EYE SKIN COLOR

(71) Applicant: Access Business Group International LLC, Ada, MI (US)

(72) Inventor: Di Qu, Ada, MI (US)

(73) Assignee: Access Business Group International LLC, A Michigan Limited Liability Company, Ada, MI (US)

( * ) Notice: Subject to any disclaimer, the term of this patent is extended or adjusted under 35 U.S.C. 154(b) by 319 days.

(21) Appl. No.: 13/793,024

(22) Filed: Mar. 11, 2013

(65) Prior Publication Data

US 2013/0245459 A1   Sep. 19, 2013

Related U.S. Application Data

(60) Provisional application No. 61/611,136, filed on Mar. 15, 2012.

(51) Int. Cl.
| | | |
|---|---|---|
| A61B 5/05 | (2006.01) | |
| A61B 5/00 | (2006.01) | |
| A61B 5/103 | (2006.01) | |
| A61B 5/026 | (2006.01) | |

(52) U.S. Cl.
CPC .......... *A61B 5/0082* (2013.01); *A61B 5/1032* (2013.01); *A61B 5/441* (2013.01); *A61B 5/0261* (2013.01)

(58) Field of Classification Search
None
See application file for complete search history.

(56) References Cited

U.S. PATENT DOCUMENTS

| | | | |
|---|---|---|---|
| 7,349,857 B2 | 3/2008 | Manzo | |
| 8,218,862 B2 | 7/2012 | Demirli et al. | |
| 8,238,623 B2 | 8/2012 | Stephan et al. | |
| 8,290,257 B2 | 10/2012 | Demirli et al. | |
| 8,319,857 B2 | 11/2012 | Qu et al. | |
| 8,358,348 B2 | 1/2013 | Mohammadi et al. | |
| 8,467,583 B2* | 6/2013 | Smith et al. ................. | 382/128 |
| 8,915,562 B2* | 12/2014 | Edgar et al. ..................... | 347/1 |
| 2003/0088437 A1 | 5/2003 | Iobst et al. | |
| 2003/0093297 A1 | 5/2003 | Schilling et al. | |
| 2004/0218810 A1* | 11/2004 | Momma ...................... | 382/162 |
| 2007/0086651 A1 | 4/2007 | Stephan et al. | |
| 2007/0258656 A1* | 11/2007 | Aarabi ......................... | 382/254 |
| 2008/0080755 A1* | 4/2008 | Payonk et al. ............... | 382/128 |
| 2008/0212894 A1 | 9/2008 | Demirli et al. | |
| 2008/0270175 A1 | 10/2008 | Rodriguez et al. | |

(Continued)

FOREIGN PATENT DOCUMENTS

| | | | |
|---|---|---|---|
| JP | 2004166801 | * | 6/2004 |
| WO | WO2012001289 | * | 1/2012 |

OTHER PUBLICATIONS

English Translation of WO2012/001289, Boulay published Jan. 2012.*
English Translation of JP2004-166801, Fuji published Jun. 2004.*

*Primary Examiner* — Jonathan Cwern
(74) *Attorney, Agent, or Firm* — Brinks Gilson & Lione

(57) ABSTRACT

Methods for quantitative measurement of under eye dark circles and other color related phenomena in eye area skin are described. The methods can be used to quantify the clinical efficacy of skin care products.

10 Claims, 15 Drawing Sheets
(15 of 15 Drawing Sheet(s) Filed in Color)

(56) References Cited

U.S. PATENT DOCUMENTS

| | | |
|---|---|---|
| 2009/0028380 A1 | 1/2009 | Hillebrand et al. |
| 2009/0196475 A1* | 8/2009 | Demirli ................. A61B 5/441 |
| | | 382/128 |
| 2009/0201365 A1 | 8/2009 | Fukuoka et al. |
| 2010/0284610 A1 | 11/2010 | Yoshikawa |
| 2011/0123703 A1 | 5/2011 | Mohammadi et al. |
| 2011/0196616 A1* | 8/2011 | Gunn .............................. 702/19 |
| 2011/0202480 A1 | 8/2011 | Maes et al. |
| 2011/0206254 A1 | 8/2011 | Patwardhan |
| 2011/0300196 A1 | 12/2011 | Mohammadi et al. |
| 2011/0301441 A1* | 12/2011 | Bandic et al. ................ 600/306 |
| 2012/0300050 A1 | 11/2012 | Korichi et al. |
| 2012/0325141 A1 | 12/2012 | Mohammadi et al. |
| 2013/0169827 A1* | 7/2013 | Santos ............... H04N 5/23229 |
| | | 348/207.1 |

\* cited by examiner

Intensity profile of ROI

- Scanning the ROI in 200 increments
- Calculate average intensity in each increment
- Obtain an intensity profile of eye area skin

Intensity profile of eye area skin

QUANTIFICATION OF UNDER-EYE SKIN COLOR

This application claims priority to U.S. Application No. 61/611,136 filed Mar. 15, 2012, the entire contents of which is incorporated herein by reference.

The present disclosure relates to methods of quantifying the clinical efficacy of skin care products and, more specifically, to methods for quantitative measurement of under eye dark circles and other color related phenomena in eye area skin.

Currently in the industry, the level of under eye dark circles is assessed using the following methods: (1) visual grading by a trained clinical grader; (2) instrumental colorimetric measurement; and (3) general image analysis method of facial photography. Of these current practices, method (1), visual grading, is a subjective method based on numbers assigned by a clinician within a ten-point scale. Accuracy and reproducibility are major concerns of this method. The instrumental colorimetric method, current method (2), is objective. However, the necessity of making a contact between instrument and the skin during a measurement has been a factor causing significant variation, specifically in the red color component of the skin. In addition, the limited accessibility in the eye area makes it difficult to have accurate measurements using commercial colorimeters. The general image analysis method, current method (3), is a method related to this invention. However, lack of specificity and automation are common drawbacks to such a method. Exact alignment of eye area features has not been addressed in these methods, which results in relatively large variation when pictures from two different time points are analyzed. Thus, there is a current need for improved methods of assessing under eye skin color that are quantitative in nature.

SUMMARY

The present disclosure provides a method of image analysis of facial digital photographs that is developed to quantitatively measure dark circles in the eye area skin. The first step is to take a digital photograph, that in one embodiment is preferably three mega pixels and above, using any commercially available digital camera. A set of color palettes with known standard color values are used when the picture is taken to provide color references for the next color correction step. The color correction process is then carried out using a set of computer algorithms. In one embodiment the color correction is performed as described in U.S. Pat. No. 8,319,857 Qu et al.

Next, a set of newly developed computer algorithms are used to automatically carry out the following steps that are important to obtaining a consistent measurement method of eye area skin: (a) detecting the locations of eyes and eyebrows from a digital picture; (b) zooming in to reveal the details of eye area features on a specified eye; (c) prompting the operator to manually confirm two fine features of the eye; (d) rotating the picture to align the eye horizontally using the identified features as reference; (e) calculating and drawing an oval shaped region of interest around the eye; (f) cropping out the region of interest as a single picture file; (g) prompting the operator to manually confirm the upper and lower boundaries of the eye; (h) calculating skin reflective intensity in a fashion which scans across the region of interest stepwise from the upper eyelid area down to the under eye area, and in one embodiment this is performed in a total of one hundred increments; (i) generating a data file from the above step to be plotted to show a skin reflective intensity profile around the eye of specific concern; (j) carrying out the same analysis of the eye to another picture of the same individual (e.g. at a different date during a clinical trial of product treatment); (k) comparing the two profiles before and after product treatment to detect changes in skin reflective intensity. Clinical efficacy can be quantified from these profiles.

Thus, the present disclosure provides a method of quantifying an under eye appearance of a human subject, comprising: detecting an eye area to be evaluated on a digital photograph of the human subject; selecting a region of interest in the eye area; calculating skin reflective intensity data within the region of interest; generating a skin reflective intensity profile from the intensity data; and quantifying a value from the intensity profile of the subject's under eye appearance. In further embodiments, the region of interest in an oval. In still further embodiments, the quantifying step (e) uses a mean square error method to quantify the under eye appearance.

The present disclosure further provides a method of determining efficacy of a skin care product on a human subject's under eye appearance, comprising: detecting an eye area to be evaluated on a digital photograph of the human subject; selecting a region of interest in the eye area; calculating skin reflective intensity data within the region of interest; generating a skin reflective intensity profile from the intensity data; and quantifying a pre-treatment value from the intensity profile of the subject's under eye appearance; treating the subject with the skin care product; repeating steps (a) through (d) after treatment with a skin care product to generate a second intensity profile; quantifying a post-treatment value of the subject's under eye appearance from the second intensity profile; and comparing the post-treatment value with the pre-treatment value to determine the efficacy of the skin care product. In still further embodiments, the quantifying steps (e) and (h) use a mean square error method to quantify the under eye appearance.

BRIEF DESCRIPTION OF THE DRAWINGS

The patent or application file contains at least one drawing executed in color. Copies of this patent or patent application publication with color drawings will be provided by the Office upon request and payment of the necessary fee.

DETAILED DESCRIPTION

Figure 1:
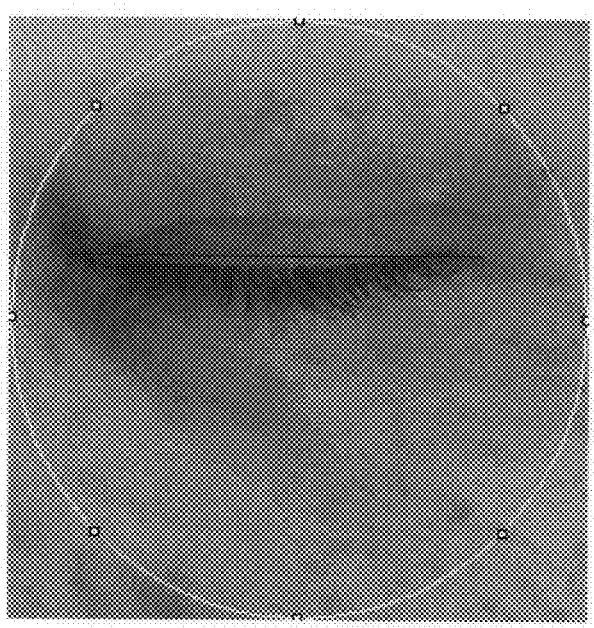
FIG. 1 illustrates alignment of eye area features using a straight line between two corners of the eye, and selection of region of interest of the eye area skin based on the identified features of the eye. The dimension of this oval shape (region of interest) is based on the dimension of the horizontal reference line and the locations of the eye and the eyebrow.

All patents, patent applications, and literature references cited in this specification are hereby incorporated herein by reference in their entirety. In case of conflict, the present description, including definitions, will control.

Under eye dark circles are a common concern of eye area skin. Currently, it is believed that they are caused by two different things: Stagnant blood flow, and hyper-pigmentation in the eye area skin. The current technologies in skin care products are to improve blood flow and to inhibit pigmentation. What is needed at this stage is an accurate, objective method to evaluate the phenomenon and to assess treatment efficacy.

Currently from the literature, we see three different methods used. Visual grading is by far the most commonly used method. However, subjectivity is the primary concern when comes to accuracy and repeatability. Colorimetric measurement is another common method. Skin contact of the instrument, however, introduces variation, particularly in the red component of skin color. It is also difficult to operate in the eye area. Image analysis of facial photographs has become more and more popular. So far, the output has been general. To our knowledge, there has not been a method specific for under eye dark circle measurement. In addition, proper color correction of digital images is often in question when using this general image analysis method.

A quantitative method was developed for measuring under eye dark circles by using a digital image of a subject and optionally applying an image analysis algorithm or algorithms. In this regard, the digital image may be obtained by a digital color video camera of a TRI-CCD type, which is available commercially from SONY; or a digital still photo or picture camera of type D70S, available commercially from NIKON. One of skill in the art, however, will understand that any suitable apparatus for obtaining a digital image of a subject may be used so long as it meets the objects of the present method.

Desirably, the digital image capturing device is configured to capture the image with at least 2 megapixels, and in other embodiments at least 3, 4, 5, 10, megapixels or more. Of course, it may be understood that the larger the number of pixels of an image to be captured, the easier the analysis may be.

In one embodiment, the digital image is obtained using a VISIA system such as those obtained by a VISIA-CR apparatus. It was an objective to use the method to assess the severity of this skin condition, to evaluate treatment efficacy, and to have a screening technology for new product development.

A digital facial image may be obtained using a digital image capturing device described above, such as for example, VISIA-CR. Then, the image is color corrected using a set of developed algorithms. One example of color correction algorithms is set forth in U.S. Pat. No. 8,319,857 to Qu et al., which is incorporated herein by reference in its entirety. Of course it is to be understood that other means of color correction may be implemented.

Next, the locations of eyebrow and the eye are detected and identified. In this regard, the measured distance between the eyebrow and the eye is used as a reference for the ROI determination. The image may also be magnified to reveal details of eye area features on a specified eye. An operator may also be prompted to manually confirm two fine features of the eye. For example, as shown in FIG. 1, a straight line connecting each corner of an eye has been imposed on the image by any known means. Thereafter, the digital image is rotated so that the straight line lies in a horizontal plane.

Alignment of the features of an eye is an important step in this process. Facial expression may change over time and therefore the alignment step is important for a consistent ROI determination. Leveling also makes it easy to scan the skin around the eye for intensity measurement.

A first region of interest, which is generally an oval shape, is created based on the dimension of the straight line and the locations of the eye and eyebrow. The digital image may then be cropped to focus substantially on the ROI. For example, FIGS. 1 and 2 show an eye area ROI where the straight line is aligned in a horizontal plane.

Figure 2:
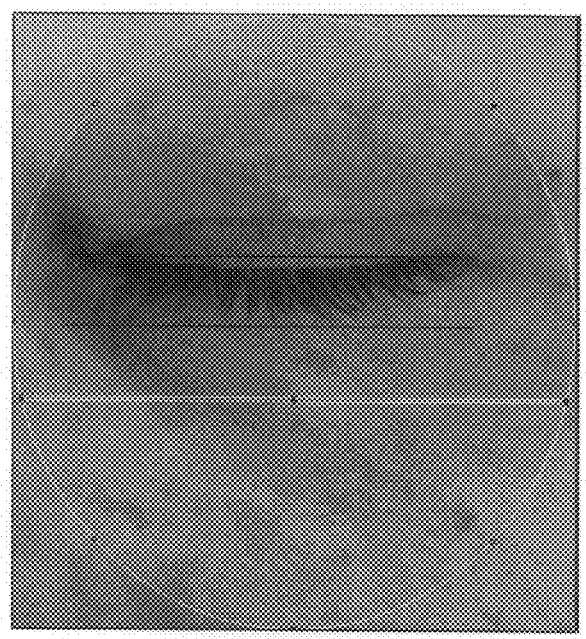
FIG. 2 illustrates measuring skin reflective intensity by scanning the region of interest from top (upper eyelid) to bottom (under eye skin) with a small elemental rectangular shape (the thin, yellow, rectangular shape in the picture). The two dark lines show the boundaries of the eye

Further, FIG. 2 shows a scan line that is moved from either the top of the ROI to the bottom or vice versa. Alternatively, as best seen in FIG. 2, a second straight line is created parallel to and spaced from the first line where the second straight line is located below the bottom eyelash. In this embodiment, the scan line is moved from the first straight line to the second straight line. In either embodiment, the scan line is moved in increments ranging from 10 to 1,000 through the selected area. It will be appreciated that the greater the number of increments, the more data that will be generated. In certain embodiments, the number of increments is from about 50 to about 500, alternatively from about 100 to 200.

Figure 7:
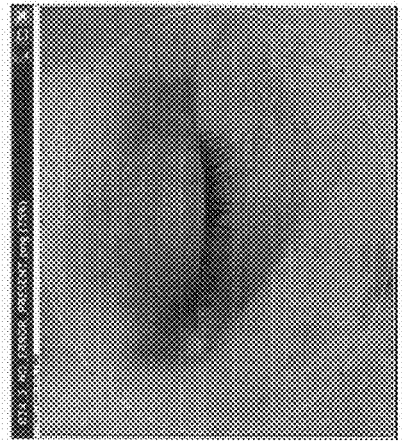
FIG. 7 illustrates the intensity profile of a region of interest ("ROI"). Scanning the ROI in two hundred increments. Calculating average intensity in each increment. Obtaining an intensity profile of eye area skin.

FIG. 7 shows an eye area ROI rotated counterclockwise 90 degrees from that shown in FIG. 1 or 2. The feature of the eye is parallel to the vertical lines. As noted above, the ROI was scanned in increments and in the embodiment depicted in FIG. 7, in two hundred increments, from the left to right as illustrated in FIG. 7. In this embodiment, the scanning is from the upper eyelid to the under eye area. Of course, it is to be understood that the scanning could proceed from right to left. In each increment, an average intensity is calculated in gray scale. Plotting it against each step obtains an intensity profile of eye area skin, as shown in FIG. 8.

Figure 8:
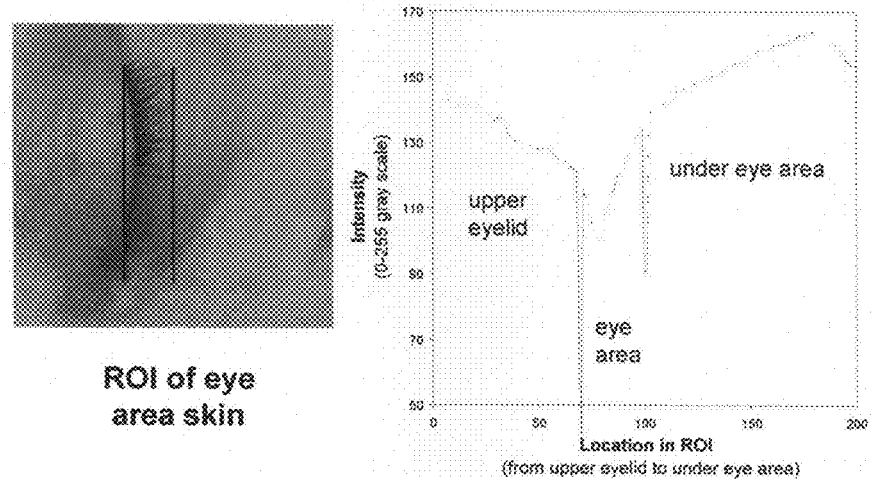
FIG. 8 illustrates intensity profile of eye area skin scanned as in FIG. 7.

The left-hand side of FIG. 8 illustrates the ROI, and the chart on the right-hand side plots the intensity profile obtained. The two sharp dips indicate the boundaries of the eye and the intensity curves on the left and the right sides of the chart correspond to the gray level of upper eyelid and the under eye skin. This profile could be adequate to describe color distribution of the eye area skin.

The present method provides an objective method which reduces or eliminates subjectivity that is associated with a visual grading method. The method provides an analysis of skin reflective intensity properties from digital photographs. It therefore eliminates the concern of instrument/skin contact inherent to the colorimetric method.

Figure 3:
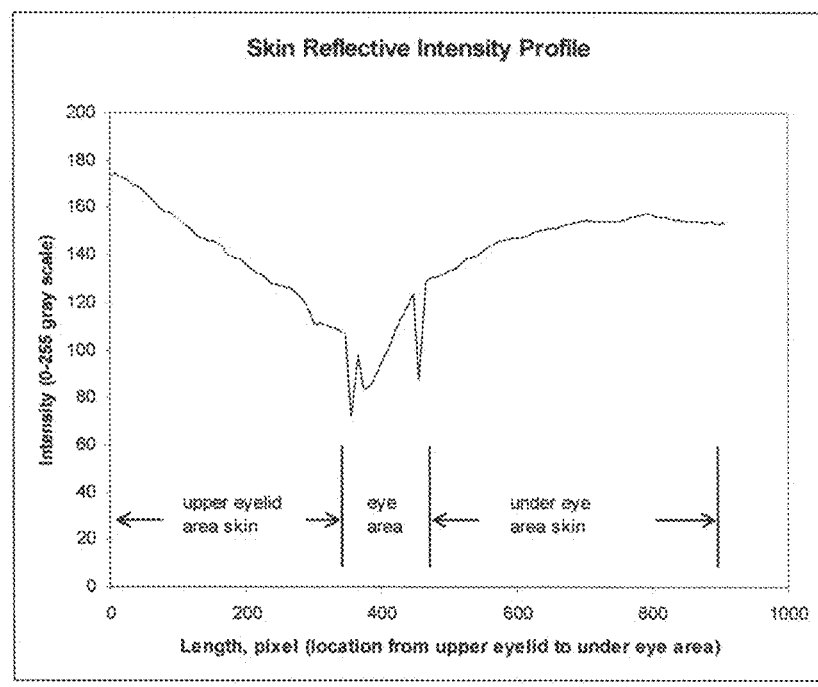
FIG. 3 illustrates an intensity profile of the eye area skin. The darkness of the eye area skin is captured in this profile. Higher intensity indicates lighter skin color. Notice the chart corresponds to the picture in FIG. 2 when it is rotated 90° counter clockwise.
Figure 4:
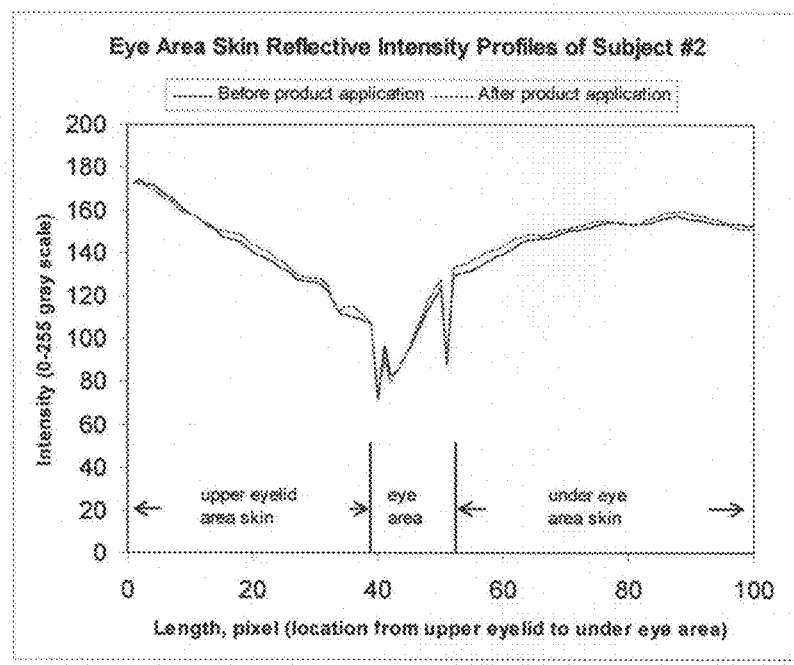
FIG. 4 illustrates intensity profiles of Subject #2 before and after product application.

The unique eye feature alignment step is an important improvement to the current general image analysis method. It is well known that features in two pictures may be slightly different when images are taken from two different points in time, particularly for those covering a long time span. The software incorporating the methods of the present method first identifies the eye area. It then provides a zoom-in image for the operator to confirm the eye area features by drawing a line connecting two corners of the eye. This line is subsequently used as a reference to rotate the image and perfectly level the eye horizontally. From there, a region of interest for eye area skin analysis is determined relative to the reference line. The ratio of skin area under evaluation is therefore fixed, relative to the features of the eye (FIG. 1). Skin reflective intensity is then measured from a scan element which is a small elemental area that scans across the region of interest from top (upper eyelid) to bottom (under eye area) in specified incremental steps, such as one hundred steps (FIG. 2). This one-dimensional scanning generates an average intensity value in each elemental area at each step, and when it is plotted against the entire scanned length, an intensity profile across the region of interest (FIG. 3) is generated. This step enables direct comparison between skin areas measured from two pictures of a person taken at two different points in time (FIG. 4).

Figure 5:
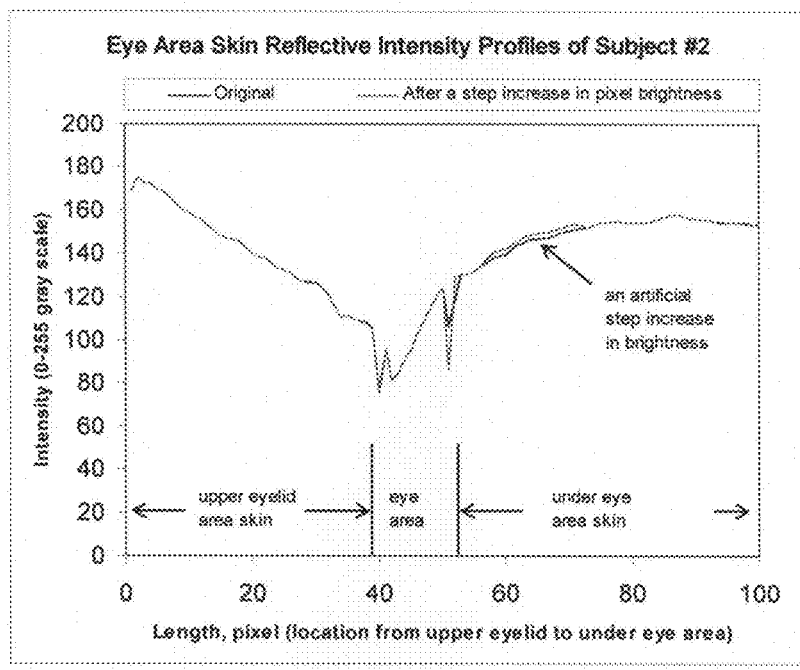
FIG. 5 illustrates intensity profiles of Subject #2 before and after an artificial increase in brightness to show the detection of step change which was not visible to the naked eye

The method of the present disclosure improves accuracy of under-eye dark circle measurements. To validate that point, an experiment was conducted on a facial picture. The intensity profile was first measured. The pixel brightness of the skin in the under-eye area of the picture was artificially increased by using image analysis software. The increase was slight, about 1.28% of the original brightness in a small area of under-eye skin, which was not visible to the naked eye in the picture. The intensity profile of the same area was measured again and now a clear step increase in skin reflective intensity is shown by the intensity profiles when two profiles are superimposed (FIG. 5).

Figure 6:
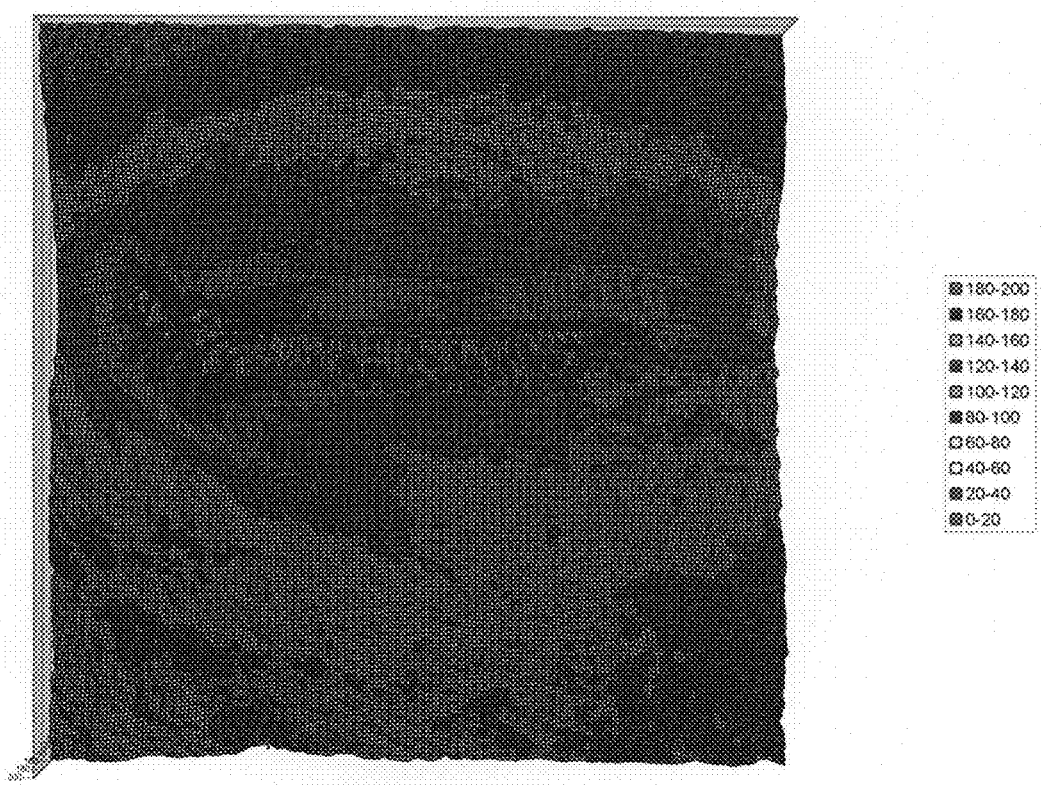
FIG. 6 illustrates intensity contours of eye area skin from a two-dimensional scan. Skin colors in the eye area can be accurately displayed based on the measured numerical values of skin reflective intensity.

The methods of the present disclosure can be practiced in a different way to achieve a totally different effect. During the steps that obtain skin reflective intensity from a picture, instead of scanning in a one-dimensional fashion, the scan can be carried out in a two-dimensional fashion over the region of interest by using a small incremental area of one or several pixels. In one embodiment, the scan is started from the upper left corner of the region of interest, scanned across the horizontal length, and then moved down one incremental step and repeated again until the entire area is covered. The result of this two-dimensional scan is a contour map of reflective intensity of the eye area skin (FIG. 6).

EXAMPLE 1

Figure 9:
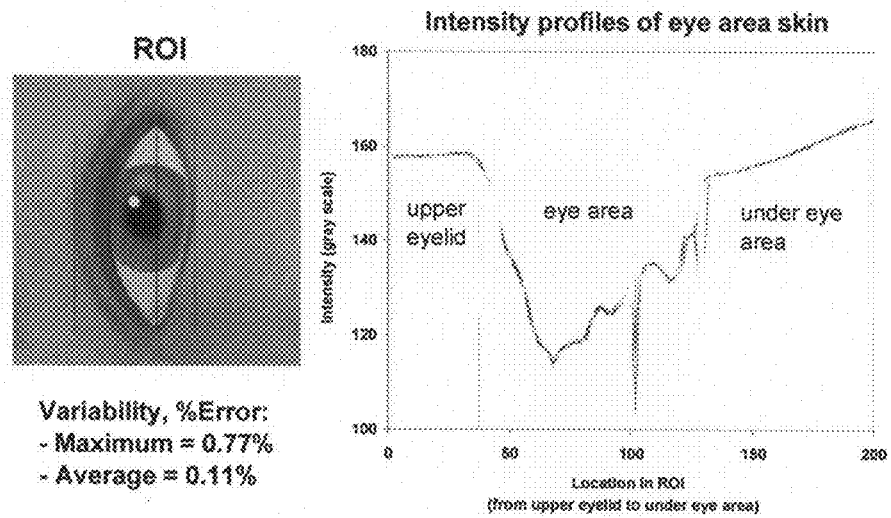
FIG. 9 illustrates the repeatability on a mannequin eye. Variability, percent error: maximum=0.77 percent, average=0.11 percent.

Repeatability on a mannequin: To validate the method, we used a mannequin as a model as illustrated in FIG. 9. The mannequin's skin color is unchanged with time, so thirty digital images were obtained, color corrected, and scanned to obtain the intensity profile. FIG. 9 shows that the method is reproducible over time.

EXAMPLE 2

Figure 10:
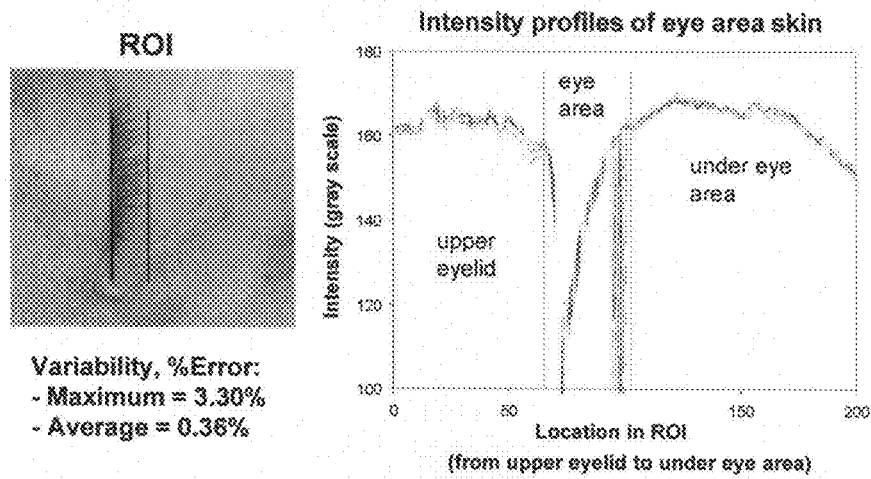
FIG. 10 illustrates the repeatability on human skin, N=30. Variability, percent error: maximum=3.30 percent, average=0.36 percent.

Repeatability on human skin: FIG. 10 illustrates the repeatability on human skin, N=30. Variability, percent error: maximum=3.30 percent, average=0.36 percent.

EXAMPLE 3

Figure 11:
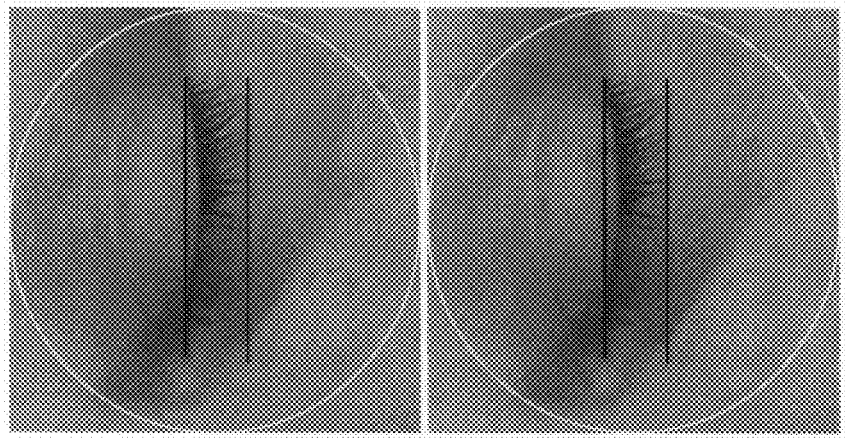
FIG. 11 illustrates sensitivity by artificially increasing the brightness value by four units out of 255 (1.57%) in a small area of the picture.
Figure 12:
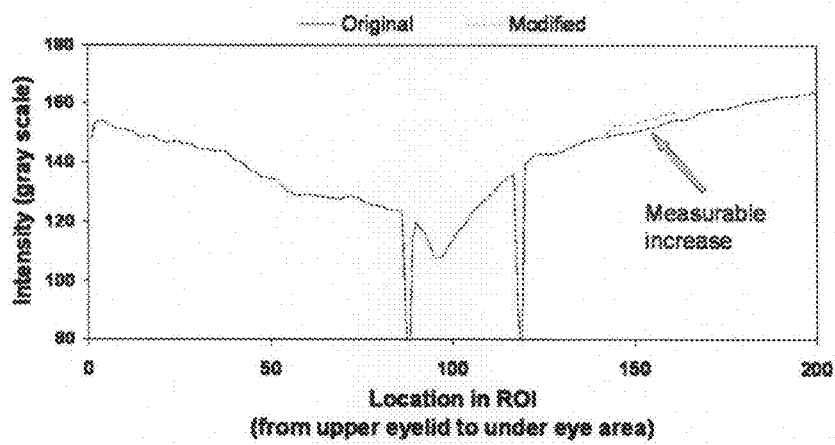
FIG. 12 illustrates the sensitivity of the intensity profile on eye area skin, when modified as discussed for FIG. 11.

Sensitivity test: FIG. 11 illustrates sensitivity by artificially increasing the brightness value by four units out of 255 (1.57%) in a small area of the picture. FIG. 12 illustrates the sensitivity of the intensity profile on eye area skin, when modified as discussed for FIG. 11.

EXAMPLE 4

Figure 13:
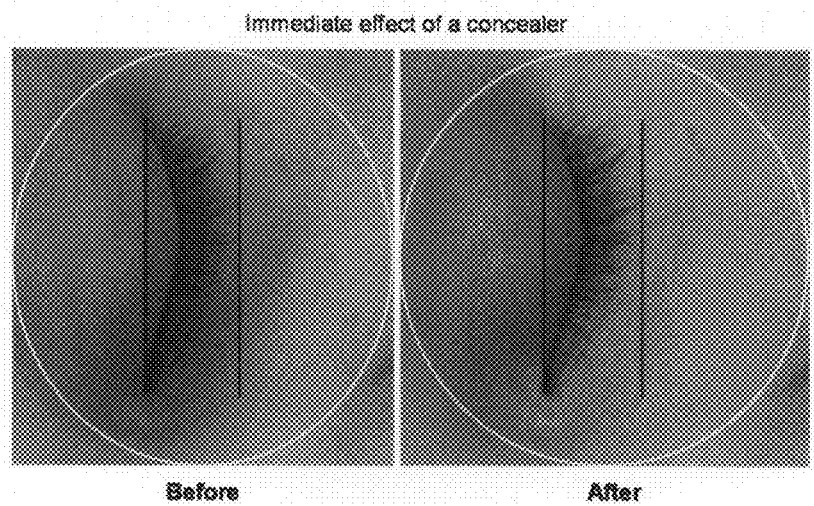
FIG. 13 illustrates quantification of product efficacy using a concealer for immediate effect.
Figure 14:
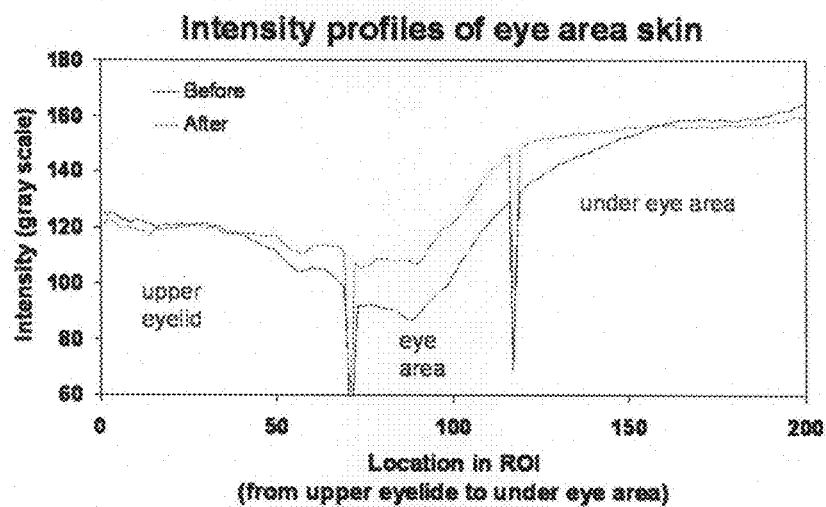
FIG. 14 illustrates intensity profiles seen with the concealer of FIG. 13.
Figure 15:
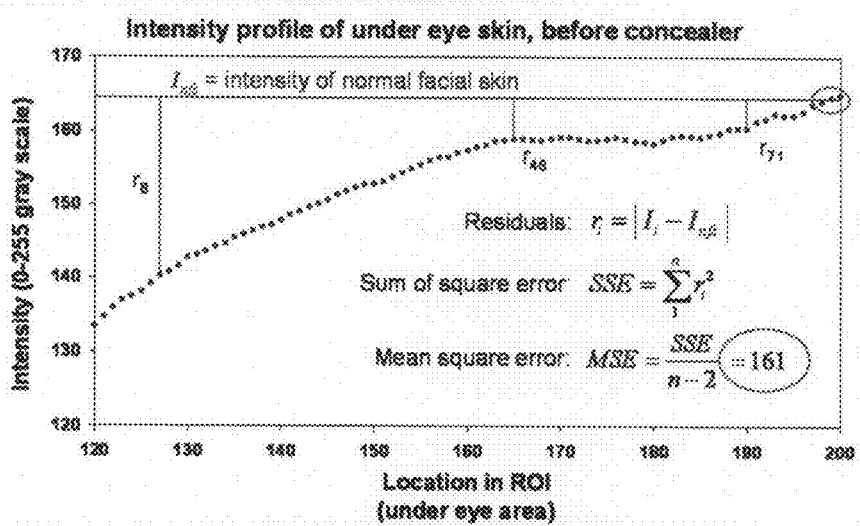
FIG. 15 illustrates the intensity profile and quantification of under the eye skin prior to using the concealer.
Figure 16:
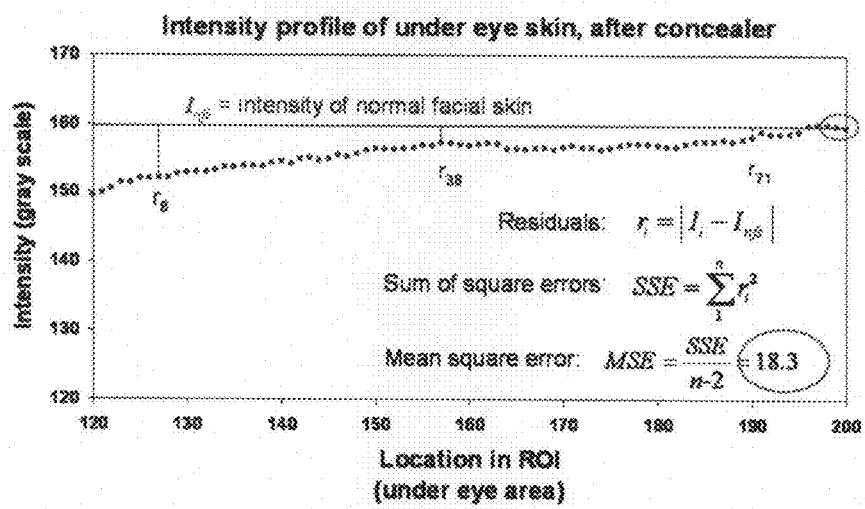
FIG. 16 illustrates the intensity profile and quantification of under the eye skin after using the concealer.
Figure 17:
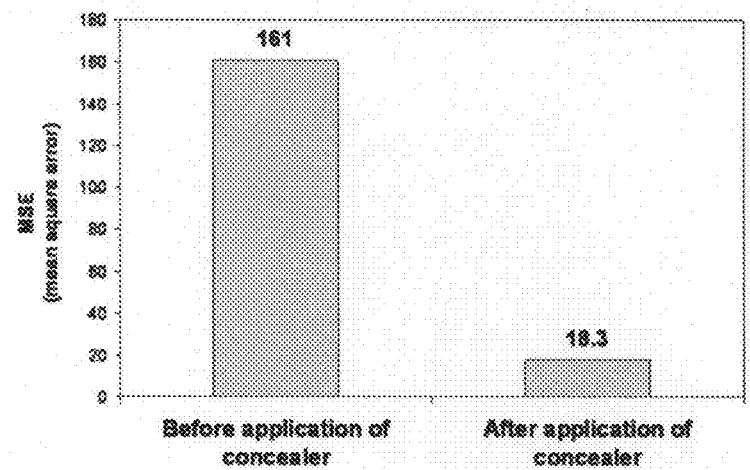
FIG. 17 illustrates a histogram plot of the mean square error ("MSE") quantification prior to application of concealer, and after application of the concealer.
Figure 18:
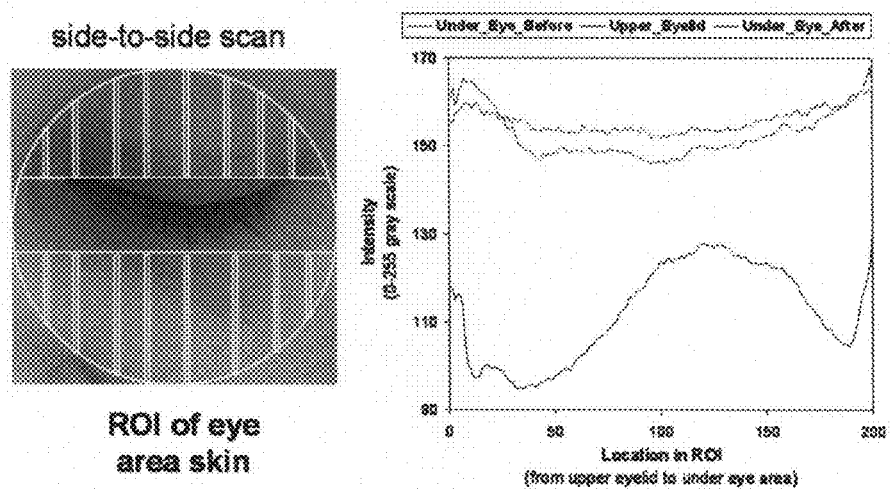
FIG. 18 illustrates an intensity profile of eye area skin with a side-to-side scan.
Figure 19:
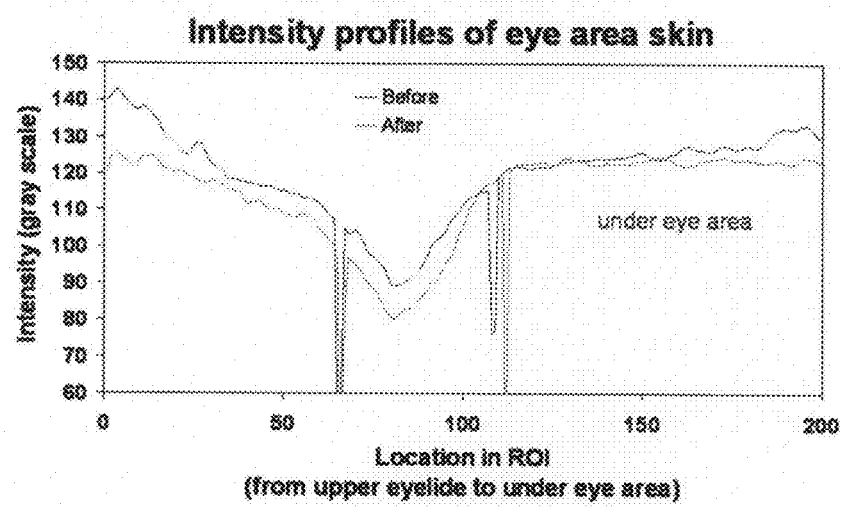
FIG. 19 illustrates the intensity profile of under the eye skin before and after laser ablation.

Quantification of product efficacy. The immediate effect of a concealer is illustrated in FIGS. 18-19. The intensity profile quantitatively describes the uniformity of eye area skin. The image analysis based technique has good precision and accuracy as a quantitative measurement method. The parameter, mean square error ("MSE"), appears to be a meaningful quantity to describe treatment efficacy of a product or dermatological procedure. FIG. 13 illustrates quantification of product efficacy using a concealer for immediate effect. FIG. 14 illustrates intensity profiles seen with the concealer of FIG. 13. FIG. 15 illustrates the intensity profile and quantification of under the eye skin prior to using the concealer. FIG. 16 illustrates the intensity profile and quantification of under the eye skin after using the concealer. FIG. 17 illustrates a histogram plot of the MSE qualification prior to application of concealer, and after application of the concealer.

EXAMPLE 5

Side-to-side scan embodiment: FIG. 18 illustrates an intensity profile of eye area skin with a side-to-side scan.

EXAMPLE 6

Figure 20:
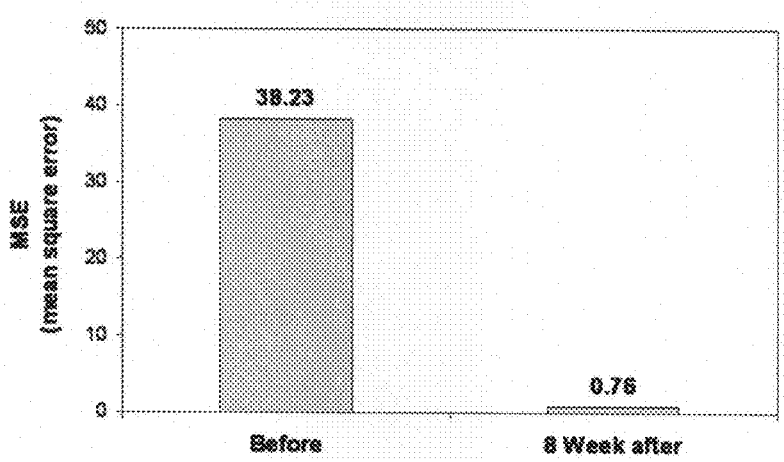
FIG. 20 illustrates quantification results showing the efficacy of laser ablation of under the eye skin, before and after laser ablation.

Laser ablation: FIG. 19 illustrates the intensity profile of under the eye skin before and after laser ablation. FIG. 20 illustrates quantification results showing the efficacy of laser ablation of under the eye skin, before and after laser ablation.

EXAMPLE 7

Figure 21:
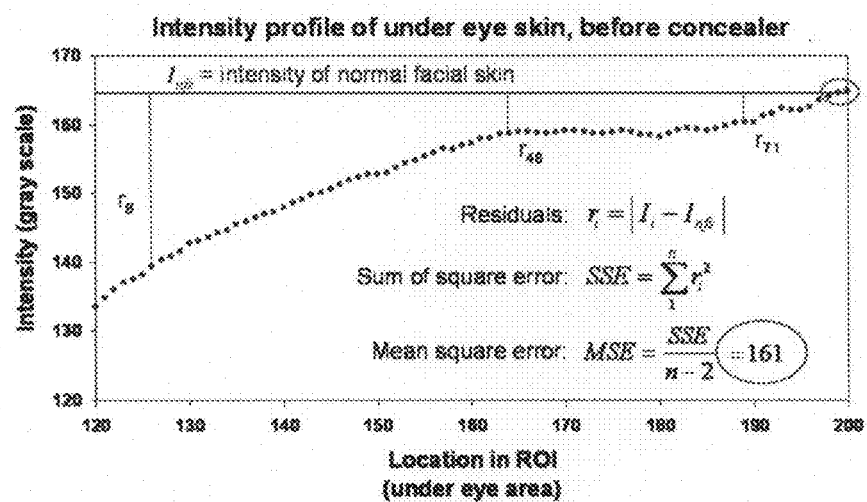
FIG. 21 illustrates quantification for defining product efficacy.

Quantification: FIG. 21 illustrates one embodiment for quantification to determine product efficacy.

EXAMPLE 8

Application of the method to the quantification of clinical efficacy of a facial essence in the under eye area. The results are seen in FIGS. 22-26.

Description of clinical study design: An in-use clinical efficacy study was conducted in an independent testing lab in Texas, U.S.A. for six weeks. Thirty four Asian and Caucasian female volunteers, ages 18-60, participated in the study. The volunteers were instructed to apply at home a test facial essence formulation to their face two times a week for 6 weeks. Facial images of each subject were taken at baseline and at week 6 using VISIA-CR in the testing lab. The images were later used to measure changes in skin color under the eye to quantify treatment efficacy of the test product.

Results: Using the method of the present invention, the following result table was obtained which includes, for each volunteer: (1) Average skin reflective intensity in the under eye area at study baseline; (2) Average skin reflective intensity in the under eye area after 6 week use of product; (3) Mean square error of the intensity profile in the under eye area at study baseline; and (4) Mean square error of the intensity profile in the under eye area after 6 weeks.

TABLE 2-I

| Subject Number | 6 week, Under Eye Area | | Baseline, Under Eye Area | | Delta | Delta |
|---|---|---|---|---|---|---|
| | Ave Int | MSE | Ave Int | MSE | Ave Int | MSE |
| 002 | 174.40 | 9.79 | 174.33 | 4.48 | 0.07 | 5.31 |
| 005 | 168.03 | 20.03 | 170.95 | 31.55 | −2.92 | −11.53 |
| 007 | 173.18 | 37.64 | 176.78 | 33.44 | −3.60 | 4.21 |
| 008 | 170.25 | 56.62 | 173.72 | 51.77 | −3.48 | 4.85 |
| 010 | 161.02 | 46.70 | 159.83 | 46.46 | 1.19 | 0.23 |
| 014 | 183.53 | 4.39 | 180.95 | 3.33 | 2.57 | 1.05 |
| 016 | 179.11 | 8.04 | 179.40 | 4.91 | −0.29 | 3.13 |
| 018 | 172.61 | 43.40 | 176.39 | 39.85 | −3.78 | 3.55 |
| 020 | 179.23 | 16.66 | 180.75 | 15.79 | −1.52 | 0.87 |
| 022 | 167.47 | 15.96 | 167.06 | 18.63 | 0.41 | −2.67 |
| 024 | 168.79 | 22.46 | 171.96 | 22.18 | −3.17 | 0.28 |
| 026 | 184.08 | 8.30 | 182.82 | 12.91 | 1.26 | −4.62 |
| 029 | 169.71 | 32.70 | 168.46 | 31.79 | 1.25 | 0.91 |
| 031 | 170.30 | 15.44 | 168.46 | 7.40 | 1.84 | 8.04 |
| 033 | 179.31 | 17.24 | 175.78 | 18.37 | 3.53 | −1.13 |
| 034 | 182.57 | 21.39 | 175.20 | 17.59 | 7.37 | 3.80 |
| 035 | 171.74 | 15.96 | 170.34 | 10.59 | 1.40 | 5.36 |
| 036 | 180.86 | 45.35 | 180.01 | 44.56 | 0.84 | 0.79 |
| 037 | 183.44 | 22.11 | 178.36 | 18.09 | 5.09 | 4.02 |
| 038 | 186.19 | 35.92 | 180.20 | 20.92 | 5.99 | 15.00 |
| 039 | 173.42 | 11.89 | 170.11 | 12.47 | 3.31 | −0.58 |

TABLE 2-I-continued

| Subject Number | 6 week, Under Eye Area | | Baseline, Under Eye Area | | Delta | Delta |
|---|---|---|---|---|---|---|
| | Ave Int | MSE | Ave Int | MSE | Ave Int | MSE |
| 040 | 178.46 | 20.35 | 176.92 | 23.49 | 1.54 | −3.14 |
| 046 | 150.66 | 67.47 | 148.97 | 63.87 | 1.69 | 3.60 |
| 048 | 173.19 | 4.93 | 172.57 | 8.82 | 0.61 | −3.89 |
| 049 | 172.72 | 46.05 | 170.55 | 45.44 | 2.17 | 0.61 |
| 054 | 180.77 | 19.29 | 175.18 | 24.52 | 5.58 | −5.22 |
| 057 | 187.15 | 6.60 | 184.75 | 11.16 | 2.40 | −4.56 |
| 060 | 172.58 | 13.87 | 163.53 | 19.81 | 9.04 | −5.93 |
| 061 | 170.36 | 2.25 | 170.03 | 2.70 | 0.32 | −0.44 |
| 062 | 181.25 | 12.56 | 180.86 | 10.46 | 0.39 | 2.10 |
| 066 | 165.73 | 15.92 | 165.27 | 18.69 | 0.46 | −2.76 |
| 067 | 179.36 | 71.05 | 178.19 | 18.76 | 1.17 | 52.29 |
| 070 | 161.84 | 13.60 | 163.47 | 19.49 | −1.63 | −5.88 |
| 072 | 175.35 | 22.84 | 170.39 | 24.84 | 4.96 | −2.00 |

Statistical Analysis

Figure 22:
FIG. 22 illustrates changes in skin reflective intensity before and after 6-week product application.

Changes in skin reflective intensity before and after 6-week product application are illustrated in FIG. 22.

t-Test: Paired Two Sample for Means

| | Baseline | 6 week |
|---|---|---|
| Average Intensity | | |
| Mean | 174.3721 | 173.0169 |
| Variance | 62.31476 | 54.19283 |
| Observations | 34 | 34 |
| Pearson Correlation | 0.92087 | |
| Hypothesized Mean Difference | 0 | |
| df | 33 | |
| t Stat | 2.56651 | |
| P (T <= t) one-tail | 0.007498 | |
| t Critical one-tail | 1.69236 | |
| P (T <= t) two-tail | 0.014997 | |
| t Critical two-tail | 2.034515 | |
| MSE (mean square error) | | |
| Mean | 24.25862 | 22.32758 |
| Variance | 319.713 | 222.3586 |
| Observations | 34 | 34 |
| Pearson Correlation | 0.824044 | |
| Hypothesized Mean Difference | 0 | |
| df | 33 | |
| t Stat | 1.111387 | |
| P (T <= t) one-tail | 0.137217 | |
| t Critical one-tail | 1.69236 | |
| P (T <= t) two-tail | 0.274434 | |
| t Critical two-tail | 2.034515 | |

Figure 23:
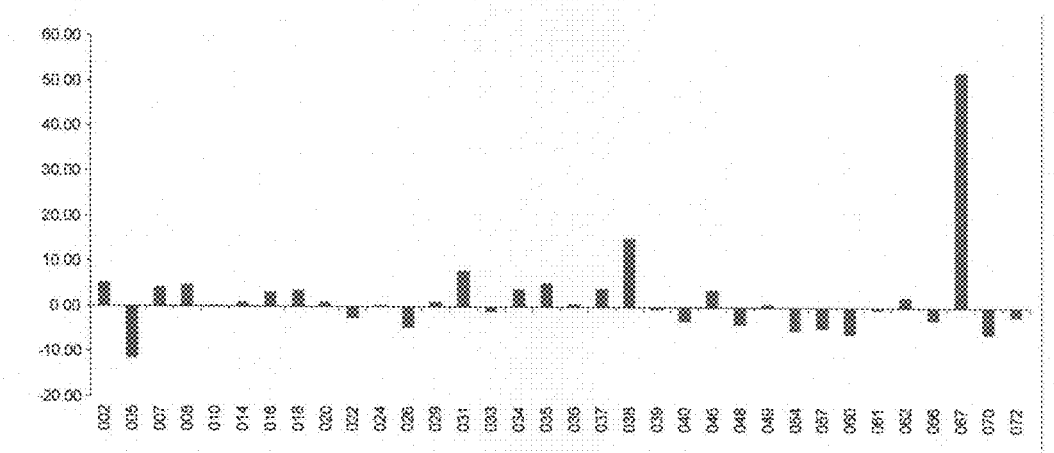
FIG. 23 illustrates changes in MSE before and after 6-week product application.
Figure 24A:
FIGS. 24A and B illustrate sample images before and after 6-week product application. Notice the makeup residue in visit 4 image (6 week) was the cause of a significant increase in MSE for subject #067.
Figure 24B:
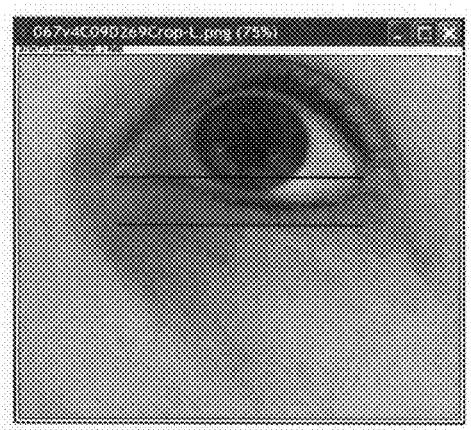

Changes in MSE (mean square error) before and after 6-week product application are illustrated in FIG. 23.

Sample images before and after six-week product application are provided in FIGS. 24A and 24B and FIGS. 25A and 25B, respectively. One skilled in the art will appreciate the presence of makeup residue in visit four image (six week) which caused a significant increase in MSE for subject 067, illustrated in FIGS. 24A and B.

Figure 25A:
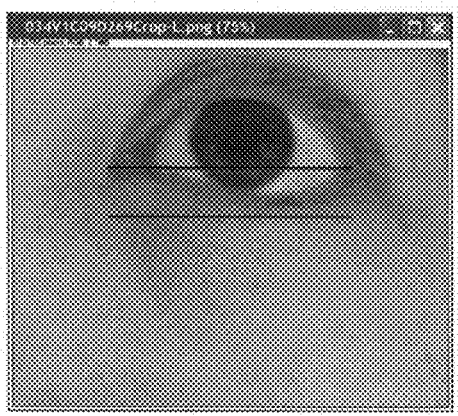
FIGS. 25A and B illustrate sample product effect of lightening the under eye area skin after product application in subject #034.
Figure 25B:
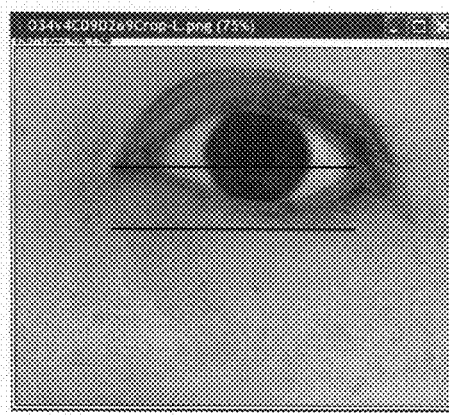
Figure 26:
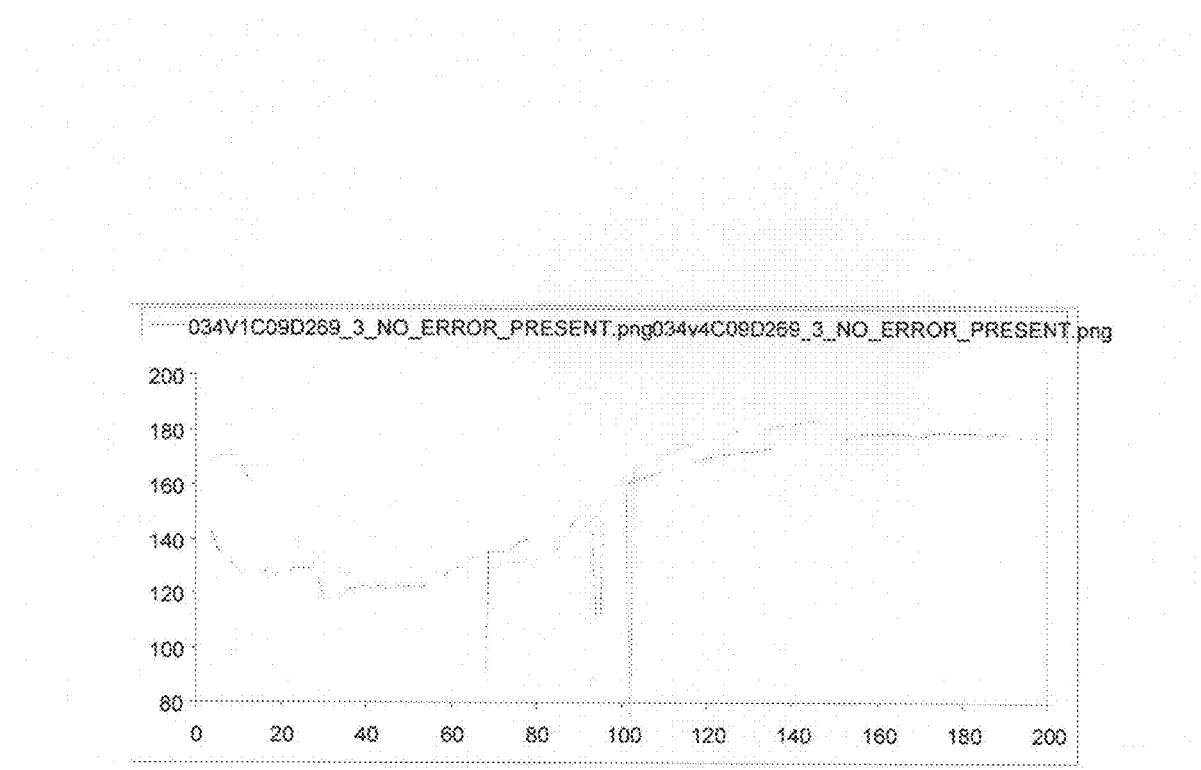
FIG. 26 illustrates the corresponding intensity profiles of the above images of Subject #034.

Sample product effect of lightening the under eye area skin after product application in Subject #034, illustrated in FIGS. 25A and 25BB. The corresponding intensity profiles of the above images of Subject #034 are illustrated in FIG. 26.

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

The invention claimed is:

1. A method of quantifying an under eye appearance of skin of a human subject, comprising:
   a. capturing a digital image of the subject with a digital image capturing device;
   b. detecting an eye area to be evaluated on the digital image of the subject;
   c. selecting a region of interest in the detected eye area based on a location of the eye and a location of a corresponding eyebrow and confirming the region of interest by drawing a horizontal reference line connecting two corners of the eye, and determining a dimension of the region of interest, wherein the dimension of the region of interest is based on a dimension of the horizontal reference line and the locations of the eye and the corresponding eyebrow;
   d. determining a series of skin reflective intensity data within the region of interest, comprising:
      defining a number of discrete slices in the region of interest; and
      determining an average skin reflective intensity in each discrete slice;
   e. generating a skin reflective intensity profile from the series of skin reflective intensity data;
   f. quantifying a value of the subject's under eye appearance of skin from the skin reflective intensity profile by calculating a mean square error (MSE):

$$\left[ MSE = \frac{SSE}{n-2} \right], \text{ wherein } \left[ SSE = \sum_{1}^{n} r_i^2 \right],$$

wherein n is the number of discrete slices, and $r_i$ is the absolute value of the difference between the average skin reflective intensity in each discrete slice and a predefined intensity.

2. The method of claim 1, wherein the region of interest is oval shaped.

3. The method of claim 1, wherein the digital image of the subject is in gray scale.

4. The method of claim 1, wherein the number of discrete slices is in the range from 10 to 1,000.

5. A method to determine efficacy of a skin care product on the subject's under eye skin appearance, comprising:
   a. performing the method of claim 1 prior to treating the subject with the skin care product to quantify a pre-treatment value of the subject's under eye appearance of skin;
   b. treating the subject with the skin care product;
   c. repeating steps (a) through (f) of claim 1 after treatment with the skin care product to generate a post-treatment skin reflective intensity profile;
   d. quantifying a post-treatment value of the subject's under eye appearance from the post-treatment skin reflective intensity profile; and
   e. comparing the post-treatment value with the pre-treatment value to determine efficacy of the skin care product.

6. A method of quantifying an under eye appearance of skin of a human subject, comprising:
   a. capturing a digital image of the subject with a digital image capturing device;
   b. detecting an eye area to be evaluated on the digital image of the subject;
   c. selecting a region of interest in the detected eye area, wherein the selecting step comprises:
      detecting the locations of eyes and eyebrows,
      zooming in to reveal the details of eye area features on a specified eye,
      prompting an operator to manually confirm two fine features of the specified eye,
      rotating the digital image to align the specified eye horizontally using the identified two features as a reference,
      calculating and drawing an oval shaped region of interest around the specified eye,
      cropping out the region of interest as a single picture file, and
      prompting the operator to manually confirm an upper boundary and a lower boundary of the specified eye;
   d. determining a series of skin reflective intensity data within the region of interest, wherein the determining step comprises:
      defining a number of discrete slices in the region of interest; and
      determining an average skin reflective intensity in each discrete slice;
   e. generating a skin reflective intensity profile from the series of skin reflective intensity data; and
   f. quantifying a value of the subject's under eye appearance of skin from the skin reflective intensity profile by calculating a mean square error (MSE) method to quantify the under eye appearance:

$$\left[ MSE = \frac{SSE}{n-2} \right], \text{ wherein } \left[ SSE = \sum_{1}^{n} r_i^2 \right],$$

wherein n is the number of discrete slices, and $r_i$ is the absolute value of the difference between the average skin reflective intensity in each discrete slice and a predefined intensity.

7. The method of claim 6, wherein the number of discrete slices is one hundred.

8. The method of claim 6, wherein the number of discrete slices is two hundred.

9. The method of claim 6, wherein the number of discrete slices is in the range from 10 to 1,000.

10. A method to determine efficacy of a skin care product on a human subject's under eye skin appearance, comprising:
   a. performing the method of claim 6 prior to treating the subject with the skin care product to quantify a pre-treatment value of the subject's under eye appearance of skin;
   b. treating the subject with the skin care product;
   c. repeating steps (a) through (f) of claim 6 after treatment with the skin care product to generate a post-treatment skin reflective intensity profile;
   d. quantifying a post-treatment value of the subject's under eye appearance from the post-treatment skin reflective intensity profile; and
   e. comparing the post-treatment value with the pre-treatment value to determine efficacy of the skin care product.

* * * * *